(12) United States Patent
Go Boncan et al.

(10) Patent No.: US 10,203,318 B2
(45) Date of Patent: Feb. 12, 2019

(54) MULTI-PURPOSE TUBE FOR OIL WELL CEMENT TESTING

(71) Applicants: Virgilio Go Boncan, Houston, TX (US); Kevin C. Madsen, Houston, TX (US); Richard F. Lukay, Houston, TX (US)

(72) Inventors: Virgilio Go Boncan, Houston, TX (US); Kevin C. Madsen, Houston, TX (US); Richard F. Lukay, Houston, TX (US)

(73) Assignee: OFI Testing Equipment, Inc., Houston, TX (US)

( * ) Notice: Subject to any disclaimer, the term of this patent is extended or adjusted under 35 U.S.C. 154(b) by 202 days.

(21) Appl. No.: 15/240,822

(22) Filed: Aug. 18, 2016

(65) Prior Publication Data

US 2017/0052168 A1 Feb. 23, 2017

Related U.S. Application Data

(60) Provisional application No. 62/207,475, filed on Aug. 20, 2015.

(51) Int. Cl.
*G01N 3/00* (2006.01)
*G01N 33/38* (2006.01)

(52) U.S. Cl.
CPC .................................. *G01N 33/383* (2013.01)

(58) Field of Classification Search
CPC ..................................................... G01N 33/383
USPC ........................................................... 73/803
See application file for complete search history.

(56) References Cited

U.S. PATENT DOCUMENTS

| 6,112,599 | A | * | 9/2000 | Maki, Jr. | G01N 29/11 73/587 |
|---|---|---|---|---|---|
| 2009/0084189 | A1 | * | 4/2009 | McMechan | G01N 3/12 73/803 |
| 2011/0061525 | A1 | * | 3/2011 | Gray | G01N 3/24 92/75 |
| 2013/0228019 | A1 | * | 9/2013 | Meadows | G01N 3/08 73/821 |
| 2014/0007695 | A1 | * | 1/2014 | Darbe | G01N 3/10 73/803 |

(Continued)

*Primary Examiner* — Helen Kwok
*Assistant Examiner* — Nashmiya Fayyaz
(74) *Attorney, Agent, or Firm* — Keeling Law, LLC; Kenneth A. Keeling; Mark S. Solomon

(57) ABSTRACT

Embodiments of a sample testing system of the present invention generally include two internally threaded caps; an externally threaded outer tube having a tapered internal bore and external circumferential grooves proximate each end thereof; an O-ring seated in each groove; and a plurality of inner tube sections cooperatively arranged to form an externally tapered inner tube structure that is disposed within the outer tube; wherein each cap is sealingly attached to an end of the outer tube via threading engagement therewith. Various embodiments utilize at least one closed-ended cap and/or at least one cap having a port extending through an end thereof, which may also incorporate a piston cavity and a piston having two circumferentially disposed O-rings. Embodiments allow for inner tube structure removal and separation of the inner tube sections for cured sample recovery. Embodiments of a method of using the system to cure a sample are also provided.

5 Claims, 11 Drawing Sheets

(56) References Cited

U.S. PATENT DOCUMENTS

2014/0202690 A1* 7/2014 Pindiprolu ......... G01N 15/0826
                                                    166/250.14

* cited by examiner

MULTI-PURPOSE TUBE FOR OIL WELL CEMENT TESTING

CROSS-REFERENCE TO RELATED APPLICATIONS

This application claims the benefit of U.S. Provisional Application No. 62/207,475 filed on Aug. 20, 2015, which application is incorporated herein by reference as if reproduced in full below.

STATEMENT REGARDING FEDERALLY SPONSORED RESEARCH OR DEVELOPMENT

Not applicable.

BACKGROUND OF THE INVENTION

Field of the Invention

The present invention generally relates to testing equipment used to measure properties of materials and chemical systems, and more specifically to an apparatus and method to subject oil well cement slurries to elevated temperatures and pressures while maintaining the shape and density of the cement slurry.

DESCRIPTION OF THE RELATED ART

In the oil and gas industry, it is necessary to understand the properties of materials used during exploration and production, and to determine how the properties are affected by temperature, pressure, and time. This is especially true of oil well cements; and while there is a slew of testing developed for standard cements, current laboratory testing of foam cement designs is difficult because of insufficient and inappropriate laboratory testing equipment.

Foam cement (also known as foamed cement) is a cement slurry comprising foaming agents and a gas, that is used to provide a low density cement system. The composition may also comprise various cement additives and/or water. Typically, the gas employed is nitrogen ($N_2$) gas, although other gases may be utilized. The foaming agent(s) employed may be selected from an assortment of commercially available materials, the selection of which is dependent on the desired properties of the cement system, as would be understood by one skilled in the art. In oil and gas wellbore drilling applications, foam cement is normally used for cementing wellbores with a low fracture gradient or for cementing across a lost-circulation zone. Traditionally, the performance of foam cement in the laboratory does not resemble its actual field properties because proper simulation conditions cannot be achieved. For example, currently practiced methods have the foam cement curing in an unconfined mold. The foam cement expands when heated in both the laboratory and actual field settings; however, under field use conditions, expansion is restricted due to hydrostatic pressure present in the wellbore, while in the laboratory, the unconfined mold allows for less restricted expansion, causing the laboratory cured cement to have a different density than designed. This less restricted expansion introduces errors to the testing.

BRIEF SUMMARY OF THE INVENTION

Embodiments of the invention generally include an apparatus comprising an outer tube and an inner tube. In various embodiments, the outer tube is constructed with open ends, a tapered interior, exterior machined threads, and an annular external circumferential groove on both ends for use with an elastomer seal, such as an O-ring. In various embodiments, the inner tube has a smooth bored inner surface, a tapered outer surface, and is split longitudinally into at least two sections.

In one embodiment of the invention, herein described as a Sealed Multi-Purpose Tube (Sealed MPT), the outer tube is sealed using two closed-ended caps. The closed-ended caps have a solid body and interior machined threads to match those on the outer tube. The Sealed MPT allows for test samples to be held at temperature without any outside pressurization.

In another embodiment, herein described as a Ported-Piston Multi-Purpose Tube (Ported-Piston MPT), the apparatus utilizes a ported cap, a piston cap, and a piston. The ported cap is similar to the sealed cap, but has a port (opening), which may be internally threaded, on the end thereof. The piston cap is similar to the ported cap, but has a small cavity to hold the piston. The piston has an outer diameter to match the inner bore of the inner tube, as well as two external circumferential grooves for use with an elastomer seal, such as an O-ring. The Ported-Piston MPT allows for test samples to be held at temperature under additional pressure, wherein the pressure is transmitted to the sample via the piston.

In another embodiment, herein described as a Piston-Sealed Multi-Purpose Tube (Piston-Sealed MPT), the apparatus utilizes a closed-ended cap, a piston cap, and a piston. In an additional embodiment, herein described as a Ported-Sealed Multi-Purpose Tube (Ported-Sealed MPT), the apparatus utilizes a ported cap and a closed-ended cap. In still another embodiment, herein described as a Ported Multi-Purpose Tube (Ported MPT), the apparatus utilizes two ported caps. In one embodiment, herein described as a Piston Multi-Purpose Tube (Piston MPT), the apparatus utilizes two piston caps.

With regard to the various embodiments of a Multi-Purpose Tube (MPT) of the present invention disclosed herein, the apparatus is adapted and configured to allow for solidification (curing) of a liquid sample under desired volume, temperature, and/or pressure control. The apparatus further allows for substantially intact recovery of the cured sample.

Other features and advantages of the invention will be apparent from the following description, the accompanying drawings, and the appended claims.

DETAILED DESCRIPTION OF EXEMPLARY EMBODIMENTS OF THE INVENTION

Figures 1, 2:
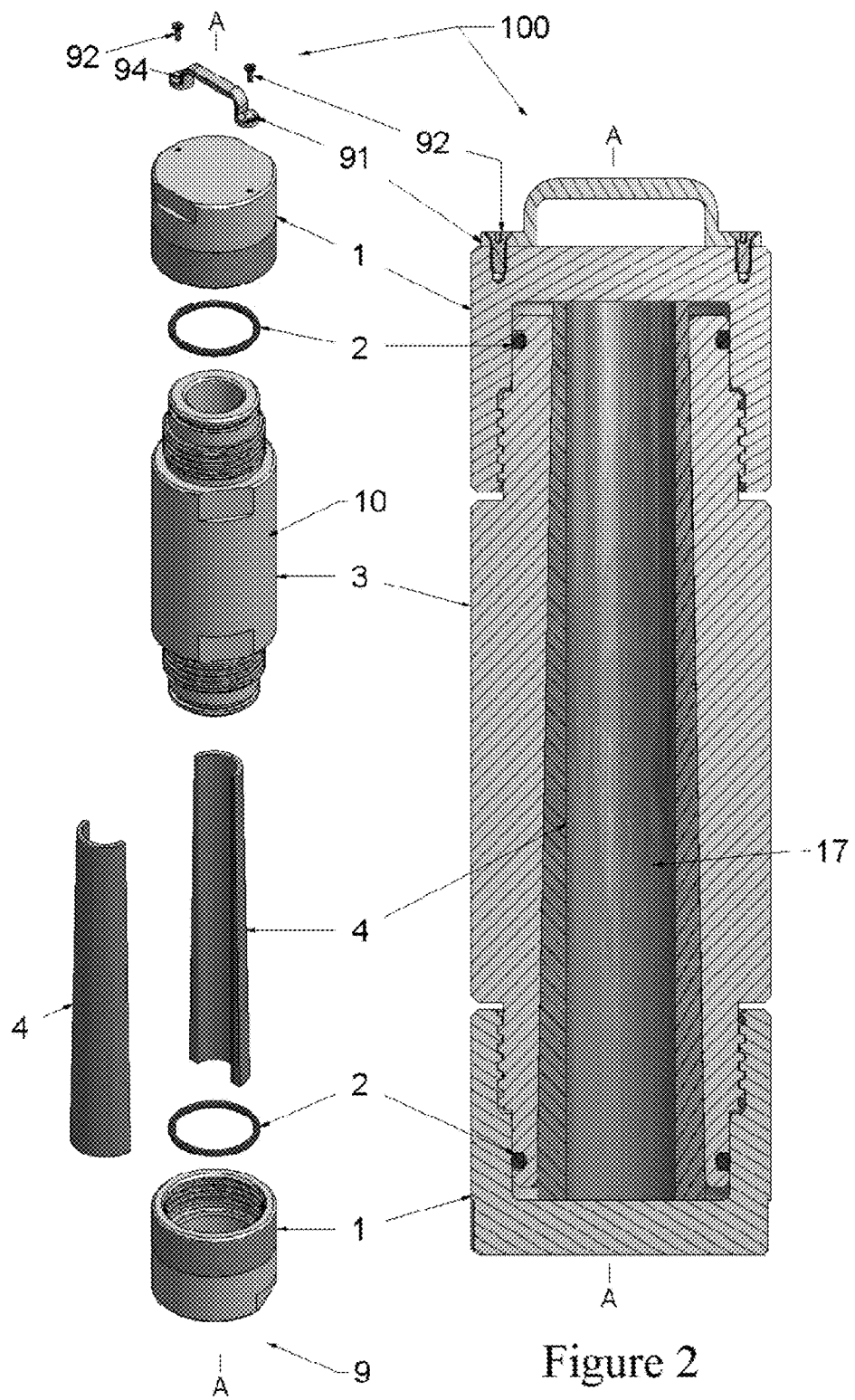
FIG. 1 is an exploded view of an embodiment of an MPT of the present invention.
FIG. 2 is a cross-sectional view of an embodiment of an MPT of the present invention.

The exemplary embodiments are best understood by referring to the drawings wherein like reference characters designate like or similar parts throughout. The directions lower, upper, top, and bottom as used in this specification are used for descriptive purposes only and other orientations are contemplated. As used herein, inner or inward means toward the axial center A-A of the MPT and outer or outward means away from the axial center A-A.

FIGS. 1 and 2 depict an embodiment 100 of a Sealed MPT of the present invention. In the depicted embodiment, Sealed MPT 100 comprises two closed-ended caps 1, two outer tube elastomer seals 2, such as O-rings, an outer tube 3, and two inner tube sections 4. In other embodiments, sealed MPT 100 may comprise more, fewer, or no outer tube O-rings 2, and/or three or more inner tube sections 4.

Figure 7:
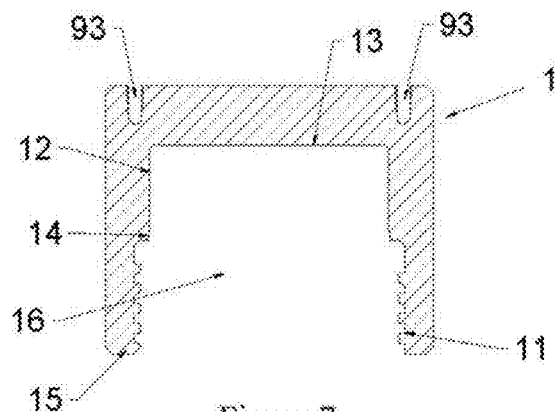
FIG. 7 is a cross-sectional view of an embodiment of a closed-ended cap of the present invention.

Embodiments of closed-ended cap 1 are shown in FIGS. 1, 2, and 7. In one embodiment, a closed-ended cap 1 comprises a substantially tubular component with an internal bore 16 open at one end and closed at the other end. Closed-ended cap 1 is configured to be removingly attachable to outer tube 3. In one embodiment, closed-ended cap 1 comprises a female connection means adapted to cooperate with a male connection means of outer tube 3, although other configurations may be utilized. In one embodiment, as shown in more detail in FIG. 7, the internal bore of closed-ended cap 1, proximate open end 15 thereof, comprises internal threading 11 to provide connectability to corresponding threading provided externally to outer tube 3, although other possible connection mechanisms are employable. In the embodiment depicted in FIG. 7, closed-ended cap 1 comprises a substantially vertical sealing surface 12 proximate internal closed end 13 thereof. Closed-ended cap 1 may comprise a beveled surface 14, intermediate sealing surface 12 and internal threading 11, that facilitates installation of open end 15 of closed-ended cap 1 over outer tube O-ring 2. In one embodiment, closed-ended cap 1 comprises a substantially cylindrical exterior, although other geometries may be utilized. Closed-ended cap 1 may comprise one or more external notches 9 or other feature to facilitate attaching closed-ended cap 1 to outer tube 3 and detaching closed-ended cap 1 therefrom. In one embodiment, shown in FIGS. 1 and 2, a closed-ended cap 1 may be equipped with a handle 91 to facilitate manipulation of the closed-ended cap 1 and/or the MPT. In one embodiment, handle 91 is attached to closed-ended cap 1 using one or more screws 92 provided through holes 94 extending through closed-ended cap 1 and engaged into threaded holes 93 (shown in FIG. 7). In other embodiments, a handle 91 may be attached to closed-ended cap 1 by other known mechanisms, or provided integral to closed-ended cap 1, as would be understood by one skilled in the art.

Embodiments of outer tube O-ring 2 are shown in FIGS. 1-4. In one embodiment, outer tube O-ring 2 is a substantially circular component utilized to increase sealability of Sealed MPT 100. Outer tube elastomer seal 2 may comprise any suitable compressible material, as would be understood by one skilled in the art. In one embodiment, an outer tube O-ring 2 comprises a fluoroelastomer (FKM) material such as Viton®. In other embodiments, an outer tube O-ring 2 comprises materials such as, but not limited to, silicone rubber (SiR); nitrile rubber (Buna-N, NBR, HNBR, HSN); polytetrafluoroethylene (PTFE), such as Teflon®; and perfluoroelastomer (FFKM), such as Kalrez®. In other embodiments, elastomer seal 2 may comprise a component such as, but not limited to, a gasket, a washer seal, or a PolyPak® seal. In one embodiment, outer tube O-ring 2 is sized to be provided external to a portion of outer tube 3, such that outer tube O-ring 2 is forced into abutment with sealing surface 12 when closed-ended cap 1 is connected to outer tube 3, thereby providing a seal there between. In other embodiments of Sealed MPT 100, alternative sealing materials such as, but not limited to, a gel material such as Teflon® paste or a thin, flexible material such as Teflon® tape, may be used in addition to, or in lieu of, one or both of outer tube O-rings 2.

Embodiments of outer tube 3 are shown in FIGS. 1-5. In one embodiment, outer tube 3 comprises a substantially cylindrical component with a tapered internal bore 32 open at both ends. As depicted in the embodiment shown in FIG. 5, tapered internal bore 32 comprises a narrower upper end 35 and a wider lower end 36. Outer tube 3 is sized and configured to accommodate inner tube sections 4 there within. Outer tube 3 is sized and adapted such that both upper end 35 and lower end 36 may each be accommodated within a closed-end cap 1. Outer tube 3 comprises an outer surface 31. In one embodiment, outer tube 3 comprises external threading 33 proximate upper end 35 and lower end 36. In one embodiment, outer tube 3 comprises an external circumferential groove 34 disposed intermediate external threading 33 and upper end 35 and/or lower end 36. Groove 34 is sized and adapted to accommodate an outer tube O-ring 2 seated there into. In one embodiment, outer tube 3 may comprise one or more external notches 10 or other feature to facilitate attaching closed-ended cap 1 to outer tube 3 and detaching closed-ended cap 1 therefrom.

Figures 3, 4:
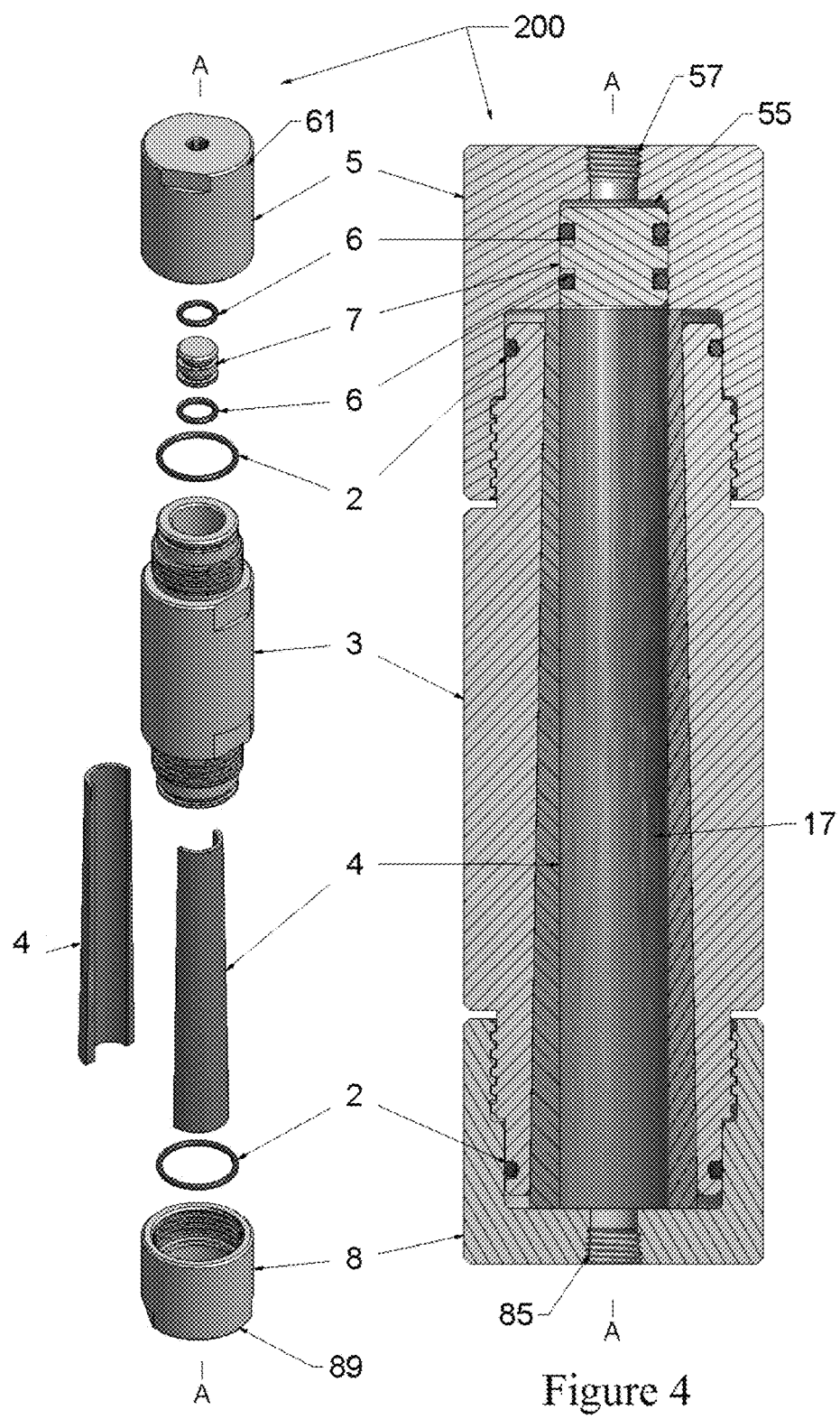
FIG. 3 is an exploded view of an embodiment of an MPT of the present invention.
FIG. 4 is a cross-sectional view of an embodiment of an MPT of the present invention.
Figures 5, 6:
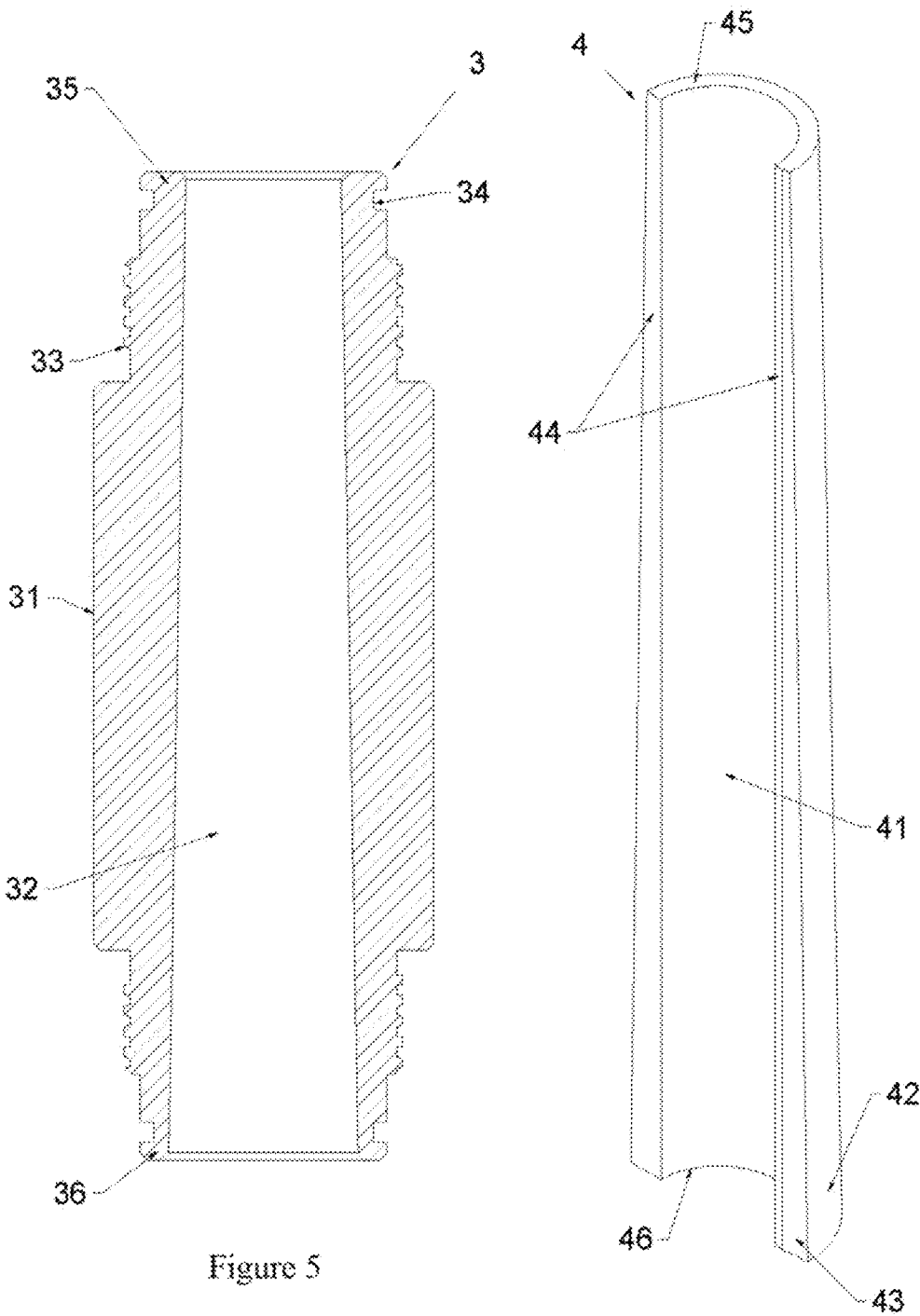
FIG. 5 is a cross-sectional view of an embodiment of an outer tube of the present invention.
FIG. 6 is a depiction of an embodiment of an inner tube section of the present invention.
Figure 6A:
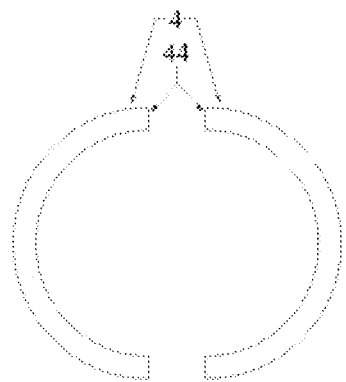
FIGS. 6A-6D are top views of embodiments of mating faces of proximate inner tube sections of the present invention.
Figure 6B:
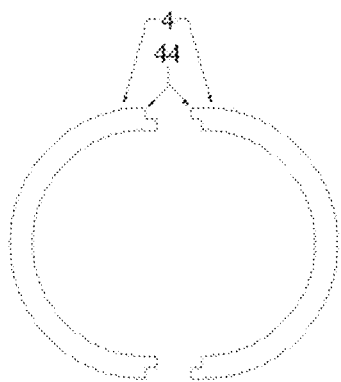
Figure 6C:
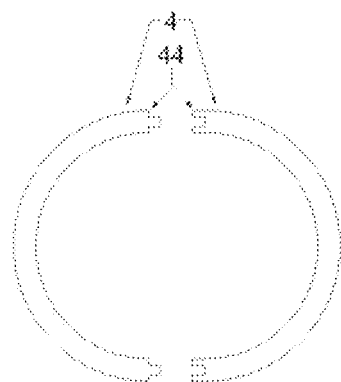
Figure 6D:
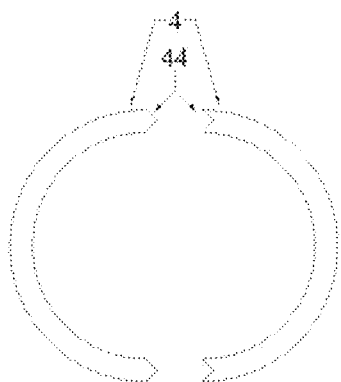

Embodiments of inner tube sections 4 are shown in FIGS. 1-4 and 6. Inner tube sections 4 are sized and configured to be cooperatively arranged to form an externally tapered, substantially annular structure. Although the embodiments shown in FIGS. 1 and 3 depict use of two inner tube sections 4, the invention is not so limited, and three or more inner tube sections 4 may be employed. Inner tube sections 4 are adapted to be combined by abutting mating faces 44 thereof, thereby forming an "inner tube structure" comprising an axial internal bore 17. In the embodiment shown in FIG. 6, each inner tube section 4 comprises a curved inner surface 41, which forms a portion of the surface of the axial internal bore 17, and a tapered outer surface 42. Cooperative arrangement of externally narrower ends 45 and externally wider ends 46 of inner tube sections 4 provides an externally tapered structure. In one embodiment, the axial internal bore 17 of the inner tube structure has a substantially equivalent diameter along the length thereof, although other geometries may be employed. When more than two inner tube sections 4 are employed, other end geometries may be employed such that an externally tapered structure is formed by cooperative arrangement of inner tube sections 4. The externally tapered structure formed by cooperative arrangement of a plurality of inner tube sections 4 is sized and configured to fit within internal bore 32 of outer tube 3. In one embodiment, one of the two mating faces 44 of the inner tube sections 4 has a beveled edge 43 adjacent to the outer surface 42 thereof. In various embodiments, mating faces 44 may comprise different but complementary geometries. In the embodiments depicted in FIGS. 6A-6D, proximate mating faces 44 are shown as in FIG. 6 (FIG. 6A), and in different but complementary geometries (FIGS. 6B-6D). In one embodiment, the length of one or more of the plurality of inner tube sections 4 is nominally greater than the length of internal bore 32 of outer tube 3.

The dimensions of the inner tube structure may be varied, and are limited only by a desired sample volume. In one embodiment, the inner tube structure has an internal diameter (ID) of about 1.00 inch (2.54 centimeters), and an axial length of about 8.00 inches (20.32 centimeters). In one embodiment, the inner tube structure has an inner tube structure length to internal diameter ratio of from about 5:1 to about 8:1. In one embodiment, the inner tube structure is sized to accommodate between about 3.38 ounces (100 milliliters) to about 8.45 ounces (250 milliliters) of sample.

FIGS. 3 and 4 depict an embodiment 200 of a Ported-Piston MPT of the present invention. In the depicted embodiment, Ported-Piston MPT 200 comprises a piston cap 5, two piston elastomer seals 6, such as O-rings, a piston 7, two outer tube O-rings 2, an outer tube 3, two inner tube sections 4, and a ported cap 8. In other embodiments, Ported-Piston MPT 200 may comprise fewer or no outer tube O-rings 2 and/or piston O-rings 6, and/or three or more inner tube sections 4. In one embodiment, Ported-Piston MPT 200 components outer tube O-ring(s) 2, outer tube 3, and inner tube sections 4 are as described above regarding Sealed MPT 100.

Figure 9:
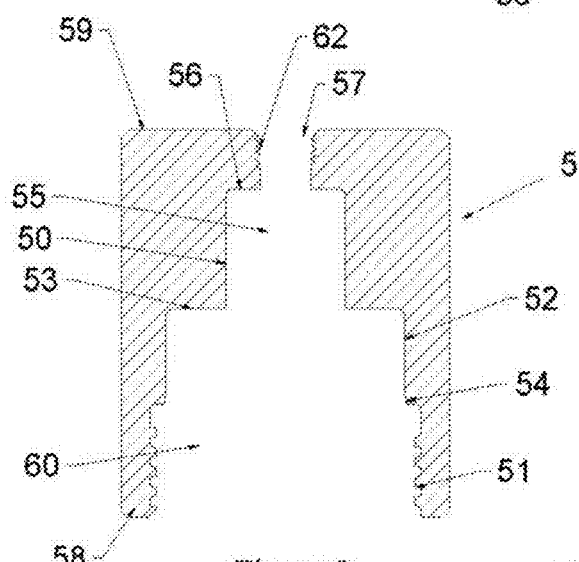
FIG. 9 is a cross-sectional view of an embodiment of a piston cap of the present invention.

Embodiments of piston cap 5 are shown in FIGS. 3, 4, and 9. In one embodiment, piston cap 5 is substantially similar to closed-ended cap 1, but additionally comprises an internally threaded port 57 (comprising internal threading 62) which extends from the exterior end surface 59 of piston cap 5 to end 56 of a piston cavity 55, fluidly connecting piston cavity 55 to the exterior of piston cap 5. In one embodiment, port 57 comprises internally tapered threading, such as but not limited to, a National Pipe Thread Taper (NPT). An open end 58 of piston cap 5 is sized and adapted to accommodate there within upper end 35 of outer tube 3. In one embodiment, piston cavity 55, having an inner surface 50, comprises a substantially tubular shaped void intermediate port 57 and an internal end 53 of the internal bore 60 of piston cap 5. In one embodiment, piston cavity 55 has a diameter substantially equal to the diameter of the axial internal bore 17 of the inner tube structure as described above. In the embodiment depicted in FIG. 9, piston cap 5 comprises a substantially vertical sealing surface 52 proximate internal end 53. Piston cap 5 may comprise a beveled surface 54, intermediate sealing surface 52 and internal threading 51, that facilitates installation of open end 58 of piston cap 5 over outer tube O-ring 2. In one embodiment, piston cap 5 comprises a substantially cylindrical exterior, although other geometries may be utilized. Piston cap 5 may comprise one or more external notches 61 or other feature to facilitate attaching piston cap 5 to outer tube 3 and detaching piston cap 5 therefrom.

Embodiments of piston O-ring 6 are shown in FIGS. 3 and 4. In one embodiment, piston O-ring 6 is a substantially circular component utilized to increase sealability of Ported-Piston MPT 200. Elastomer seal 6 may comprise any suitable compressible material, as would be understood by one skilled in the art. In one embodiment, a piston O-ring 6 comprises a fluoroelastomer (FKM) material such as Viton®. In other embodiments, a piston O-ring 6 comprises materials such as, but not limited to, silicone rubber (SiR); nitrile rubber (Buna-N, NBR, HNBR, HSN); polytetrafluoroethylene (PTFE), such as Teflon®; and perfluoroelastomer (FFKM), such as Kalrez®. In other embodiments, elastomer seal 6 may comprise a component such as, but not limited to, a gasket, a washer seal, or a PolyPak® seal. In one embodiment, piston O-ring 6 is sized to be provided external to a portion of piston 7, such that piston O-ring 6 is forced into abutment with the internal surface of piston cavity 55 when piston cap 5, containing piston 7 disposed in piston cavity 55 there within, is connected to outer tube 3, thereby providing a seal between piston 7 and piston cap 5. In other embodiments of Ported-Piston MPT 200, alternative sealing materials such as, but not limited to, a gel material such as Teflon® paste or a thin, flexible material such as Teflon® tape, may be used in addition to, or in lieu of, one or both of piston O-rings 6. In the embodiment depicted in FIGS. 3 and 4, two piston O-rings 6 are employed, however, the invention is not so limited and more, fewer, or no O-rings 6 may be utilized to practice the present invention.

Figure 10:
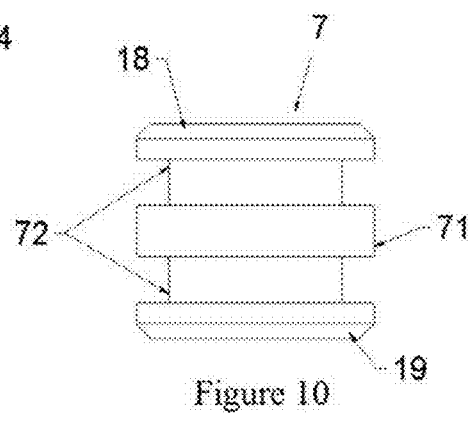
FIG. 10 is a depiction of an embodiment of a piston of the present invention.

Embodiments of piston 7 are shown in FIGS. 3, 4, and 10. In one embodiment, piston 7 comprises a substantially cylindrical component, comprising a top surface 18 and a bottom surface 19, that is sized and adapted to be accommodated within piston cavity 55. In one embodiment, piston 7 has an outer surface 71 which contains one or more circumferential external grooves 72 that are sized and adapted to accommodate a piston O-ring 6 seated there into.

Figure 8:
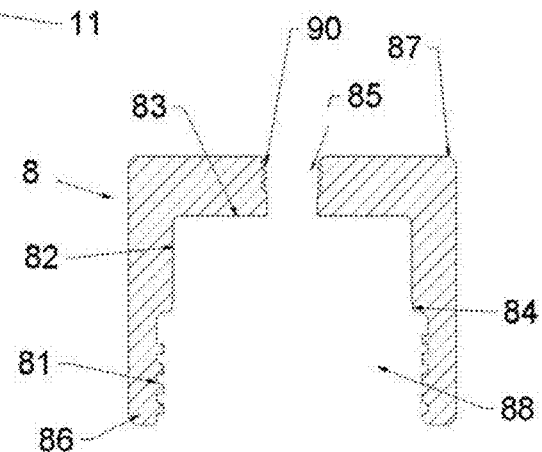
FIG. 8 is a cross-sectional view of an embodiment of a ported cap of the present invention.

Embodiments of ported cap 8 are shown in FIGS. 3, 4, and 8. In one embodiment, ported cap 8 is substantially similar to closed-ended cap 1, but additionally comprises an internally threaded port 85 (comprising internal threading 90) which extends from the exterior end surface 87 of ported cap 8 through an internal end 83 of an internal bore 88 of ported cap 8. Threaded port 85 provides fluid communication between the exterior of ported cap 8 and the internal bore 88 of ported cap 8. In one embodiment, port 85 comprises internally tapered threading, such as but not limited to, a National Pipe Thread Taper (NPT). An open end 86 of ported cap 8 is sized and adapted to accommodate there within lower end 36 of outer tube 3. In the embodiment depicted in FIG. 8, ported cap 8 comprises a substantially vertical sealing surface 82 proximate internal end 83 of internal bore 88 thereof. Ported cap 8 may comprise a beveled surface 84, intermediate sealing surface 82 and internal threading 81, that facilitates installation of open end 86 of ported cap 8 over outer tube O-ring 2. In one embodiment, ported cap 8 comprises a substantially cylindrical exterior, although other geometries may be utilized. Ported cap 8 may comprise one or more external notches 89 or other feature to facilitate attaching ported cap 8 to outer tube 3 and detaching ported cap 8 therefrom.

In another embodiment (not shown), herein described as a Piston-Sealed MPT, the device comprises a closed-ended cap 1, two outer tube O-rings 2, an outer tube 3, two inner tube sections 4, a piston cap 5, two piston O-rings 6, and a piston 7. In other embodiments, a Piston-Sealed MPT may comprise fewer or no outer tube O-rings 2 and/or piston O-rings 6, and/or three or more inner tube sections 4. In one embodiment, Piston-Sealed MPT components closed-ended cap 1, outer tube O-ring(s) 2, outer tube 3, and inner tube sections 4 are as described above regarding Sealed MPT 100, and Piston-Sealed MPT components piston cap 5, piston O-ring(s) 6, and piston 7 are as described above regarding Ported-Piston MPT 200.

In another embodiment (not shown), herein described as a Ported-Sealed MPT, the device comprises a closed-ended cap 1, two outer tube O-rings 2, an outer tube 3, two inner tube sections 4, and a ported cap 8. In other embodiments, a Ported-Sealed MPT may comprise fewer or no outer tube O-rings 2 and/or three or more inner tube sections 4. In one embodiment, Ported-Sealed MPT components closed-ended cap 1, outer tube O-ring(s) 2, outer tube 3, and inner tube sections 4 are as described above regarding Sealed MPT 100, and Ported-Sealed MPT component ported cap 8 is as described above regarding Ported-Piston MPT 200.

In another embodiment (not shown), herein described as a Ported MPT, the device comprises two ported caps 8, two outer tube O-rings 2, an outer tube 3, and two inner tube sections 4. In other embodiments, a Ported MPT may comprise fewer or no outer tube O-rings 2 and/or three or more inner tube sections 4. In one embodiment, Ported MPT components outer tube O-ring(s) 2, outer tube 3, and inner tube sections 4 are as described above regarding Sealed MPT 100, and Ported MPT components ported caps 8 are as described above regarding Ported-Piston MPT 200.

In another embodiment (not shown), herein described as a Piston MPT, the device comprises two piston caps 5, two outer tube O-rings 2, an outer tube 3, two inner tube sections 4, four piston O-rings 6, and 2 pistons 7. In other embodiments, a Piston-MPT may comprise fewer or no outer tube O-rings 2 and/or piston O-rings 6, and/or three or more inner tube sections 4. In one embodiment, Piston MPT components outer tube O-ring(s) 2, outer tube 3, and inner tube sections 4 are as described above regarding Sealed MPT 100, and Piston MPT components piston cap 5, piston O-ring(s) 6, and piston 7 are as described above regarding Ported-Piston MPT 200.

Various embodiments of Multi-Purpose Tube systems of the present invention may be provided in alternative manners of utilizing the system components described herein. As an example only, embodiments in which a closed-ended cap 1 is provided may alternatively comprise, in lieu of the closed-ended cap 1, a piston cap 5, including or not including a piston 7 disposed there within, and with or without fluid sealing of port 57 of the piston cap 5 as applicable to provide a sealed system; or in lieu of the closed-ended cap 1, a ported cap 8 with fluid sealing of port 85 of ported cap 8. As one skilled in the art would understand, other described components of embodiments of the Multi-Purpose Tube systems may be combined and/or interchanged to provide an apparatus for and means of testing samples according to the present invention.

In various MPT embodiments, closed-ended cap(s) 1, outer tube 3, inner tube sections 4, piston cap 5, piston 7, and/or ported cap(s) 8 comprise the same or different materials. Such materials include, but are not limited to, materials comprising metals, such as steel and aluminum; and metal alloys, such as brass and nickel alloys including Inconel®. In one embodiment, the material of construction for one or more of these components comprises stainless steel. In one embodiment, MPT apparatuses described herein can be utilized to expose test samples to temperatures of between about 40 degrees Fahrenheit (4 degrees Celsius) and about 400 degrees Fahrenheit (204 degrees Celsius). In one embodiment, MPT apparatuses described herein can be utilized to expose test samples to pressures up to about 3000 psi (20.68 MPa). The dimensional and operational parameters described herein are exemplary only, however, and one skilled in the art would understand the invention is not so limited.

Operation

Referring again to FIGS. 1, 2, and 5, in an exemplary operation of Sealed MPT 100, an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form the inner tube structure. The end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, a closed-ended cap 1 is attached onto the lower end 36 of outer tube 3 by means of engagement of interior threads 11 of the closed-ended cap 1 and the exterior threads 33 of outer tube 3, thereby forming a seal between the proximate outer tube O-ring 2 and sealing surface 12 of that closed-ended cap 1. Also thereby, internal closed end 13 of closed-ended cap 1 contacts the bottom end of the inner tube structure and biases the inner tube structure upward into outer tube 3. Such biasing creates a seal between mating surfaces 44 of inner tube sections 4. In one embodiment, a test sample (not shown) is then placed into the upper end of the inner tube structure, which is disposed within outer tube 3. Another closed-ended cap 1 is then attached onto the upper end 35 of outer tube 3 by means of threaded engagement of interior threads 11 of that closed-ended cap 1 and the exterior threads 33 of outer tube 3, thereby forming a seal between the proximate outer tube O-ring 2 and sealing surface 12 of that closed-ended cap 1. In one embodiment, the Sealed MPT 100 is then heated to "cure" the sample by means as are known in the art.

Upon conclusion of the heat treatment, the Sealed MPT 100 can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

Referring again to FIGS. 3 and 4, in an exemplary operation of Ported-Piston MPT 200, an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form the inner tube structure. In one embodiment, the end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, ported cap 8 is attached onto the lower end 36 of outer tube 3 by means of engagement of interior threads 81 of ported cap 8 and exterior threads 33 of outer tube 3, thereby forming a seal between the proximate outer tube O-ring 2 and sealing surface 82 of ported cap 8. Also thereby, internal end 83 of internal bore 88 of ported cap 8 contacts the bottom end of the inner tube structure and biases the inner tube structure upward into outer tube 3. Such biasing creates a seal between mating surfaces 44 of inner tube sections 4. A piston O-ring 6 is installed in each external groove 72 of piston 7, and piston 7 thus equipped is installed into piston cavity 55 of piston cap 5, thereby forming two annular seals between piston 7 and the inner surface 50 of piston cavity 55 of piston cap 5. Piston cap 5, containing the piston O-rings 6 equipped piston 7, is then attached onto the upper end 35 of outer tube 3 by means of threaded engagement of interior threads 51 of piston cap 5 and exterior threads 33 of outer tube 3, thereby forming a seal between the proximate outer tube O-ring 2 and sealing surface 52 of piston cap 5. In one embodiment, a desired fluid pressure is then applied, via port 57 of piston cap 5, to the top surface of piston 7, using an external fluid pressure source (not shown) connected to a fluid communication system (not shown), which comprises an external threading sized and adapted to engage the internal threading 62 of port 57, threadingly engaged with port 57. The applied fluid pressure forces piston 7 to the bottom of the inner tube structure, proximate ported cap 8. In one embodiment, while such pressure is being applied to piston 7, pressurized sample material (not shown) is then provided into the inner tube structure, which is disposed within outer tube 3, through port 85 of ported cap 8, utilizing an external, pressurized source of test sample material (not shown) connected to a fluid communication system (not shown), which comprises an external threading sized and adapted to engage the internal threading 90 of port 85, threadingly engaged with port 85. The sample material is provided at a pressure at least sufficient to force piston 7 upward in the inner tube structure and force the top end of piston 7 into abutment with end 56 of piston cavity 55 when the inner tube structure has been filled with pressurized test sample. At this point, in one embodiment, two pressure sealing operations are performed. In one operation, fluid flow out of Ported-Piston MPT 200 through port 57 of piston cap 5 is prevented. This may be accomplished, for example, by manipulation, either manual or automated, of a flow control device (not shown), such as a valve, of the fluid communication system attached to port 57, or by disconnecting the fluid communication system attached to port 57 and attaching an externally threaded plug (not shown) into port 57. In another operation, the provision of pressurized test sample to Ported-Piston MPT 200 is discontinued, and fluid flow out of Ported-Piston MPT 200 through port 85 of ported cap 8 is prevented. This may be accomplished, for example, by manipulation, either manual or automated, of a flow control device (not shown), such as a valve, of the fluid communication system attached to port 85, or by disconnecting the fluid communication system attached to port 85 and attaching an externally threaded plug (not shown) into port 85. In one embodiment, the Ported-Piston MPT 200 is then heated to "cure" the sample by means as are known in the art.

Upon conclusion of the heat treatment, the Ported-Piston MPT 200 can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

In an exemplary operation of a Piston-Sealed MPT (not shown), an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form an inner tube structure. The end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, a closed-ended cap 1 is attached onto the lower end 36 of outer tube 3 by means of engagement of interior threads 11 of closed-ended cap 1 and exterior threads 33 of outer tube 3, thereby forming a seal between the proximate outer tube O-ring 2 and sealing surface 12 of closed-ended cap 1. Also thereby, internal closed end 13 of closed-ended cap 1 contacts the bottom end of the inner tube structure and biases the inner tube structure upward into outer tube 3. Such biasing creates a seal between mating surfaces 44 of inner tube sections 4. In one embodiment, a test sample (not shown) is then placed into the upper end of the inner tube structure, which is disposed within outer tube 3. In one embodiment, a piston O-ring 6 is installed in each external groove 72 of piston 7, and piston 7 thus equipped is installed into piston cavity 55 of piston cap 5, thereby forming two seals between piston 7 and the inner surface 50 of piston cavity 55 of piston cap 5. Piston cap 5, containing the piston O-rings 6 equipped piston 7, is then attached onto the upper end 35 of outer tube 3 by means of threaded engagement of interior threads 51 of piston cap 5 and exterior threads 33 of outer tube 3, thereby forming a seal between the proximate outer tube O-ring 2 and sealing surface 52 of piston cap 5. In one embodiment, a desired fluid pressure is then applied, via port 57 of piston cap 5, to the top surface of piston 5, using an external fluid pressure source (not shown) connected to a fluid communication system (not shown), which comprises an external threading sized and adapted to engage the internal threading 62 of port 57, threadingly engaged with port 57. At this point, a pressure sealing operation is performed. In this operation, fluid flow out of the Piston-Sealed MPT through port 57 of piston cap 5 is prevented. This may be accomplished, for example, by manipulation, either manual or automated, of a flow control device (not shown), such as a valve, of the fluid communication system attached to port 57, or by disconnecting the fluid communication system attached to port 57 and attaching an externally threaded plug (not shown) into port 57. In one embodiment, the Piston-Sealed MPT is then heated to "cure" the sample by means as are known in the art.

Upon conclusion of the heat treatment, the Piston-Sealed MPT can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

In an exemplary operation of a Ported-Sealed MPT (not shown), an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form an inner tube structure. The end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, a closed-ended cap 1 is attached onto the lower end 36 of outer tube 3 by means of engagement of interior threads 11 of closed-ended cap 1 and exterior threads 33 of outer tube 3, thereby forming a seal between the proximate outer tube O-ring 2 and sealing surface 12 of closed-ended cap 1. Also thereby, internal closed end 13 of closed-ended cap 1 contacts the bottom end of the inner tube structure and biases the inner tube structure upward into outer tube 3. Such biasing creates a seal between mating surfaces 44 of inner tube sections 4. In one embodiment, a test sample (not shown) is then placed into the upper end of the inner tube structure, which is disposed within outer tube 3. A ported cap 8 is then attached onto the upper end 35 of outer tube 3 by means of threaded engagement of interior threads 81 of the ported cap 8 and the exterior threads 33 of outer tube 3, thereby forming a seal between the proximate outer tube O-ring 2 and sealing surface 82 of the ported cap 8. In one embodiment, a desired fluid pressure is then applied, via port 85 of ported cap 8, to internal bore 17 of the inner tube structure, using an external fluid pressure source (not shown) connected to a fluid communication system (not shown), which comprises an external threading sized and adapted to engage the internal threading 90 of port 85, threadingly engaged with port 85. At this point, a pressure sealing operation is performed. In this operation, fluid flow out of the Ported-Sealed MPT through port 85 of ported cap 8 is prevented. This may be accomplished, for example, by manipulation, either manual or automated, of a flow control device (not shown), such as a valve, of the fluid communication system attached to port 85, or by disconnecting the fluid communication system attached to port 85 and attaching an externally threaded plug (not shown) into port 85. In one embodiment, the Ported-Sealed MPT is then heated to "cure" the sample by means as are known in the art.

Upon conclusion of the heat treatment, the Ported-Sealed MPT can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

In an exemplary operation of a Ported MPT (not shown), an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form an inner tube structure. The end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, one ported cap 8 is then attached onto the lower end 36 of outer tube 3 by means of threaded engagement of interior threads 81 of that ported cap 8 and the exterior threads 33 of outer tube 3, thereby forming a seal between the proximate outer tube O-ring 2 and sealing surface 82 of the ported cap 8. Also thereby, internal end 83 of internal bore 88 of ported cap 8 contacts the bottom end of the inner tube structure and biases the inner tube structure upward into outer tube 3. Such biasing creates a seal between mating surfaces 44 of inner tube sections 4. In one embodiment, a second ported cap 8 is then attached onto the upper end 35 of outer tube 3 by means of threaded engagement of interior threads 81 of that ported cap 8 and the exterior threads 33 of outer tube 3, thereby forming a seal between the proximate outer tube O-ring 2 and sealing surface 82 of the ported cap 8 In one embodiment, pressurized sample material (not shown) is then provided into the inner tube structure, which is disposed within outer tube 3, through port 85 of the ported cap 8 attached to the lower end 36 of outer tube 3, utilizing an external, pressurized source of test sample material (not shown) connected to a fluid communication system (not shown), which comprises an external threading sized and adapted to engage the internal threading 90 of port 85, threadingly engaged with port 85. In one embodiment, when a desired amount of sample material (not shown) has been provided into the inner tube structure, fluid flow out of the Ported MPT through port 85 of ported cap 8 attached to the lower end 36 of outer tube 3 is prevented. This may be accomplished, for example, by manipulation, either manual or automated, of a flow control device (not shown), such as a valve, of the fluid communication system attached to port 85, or by disconnecting the fluid communication system attached to port 85 and attaching an externally threaded plug (not shown) into port 85. In one embodiment, a desired fluid pressure is then applied, via port 85 of the ported cap 8 attached to the upper end 35 of outer tube 3, to internal bore 17 of the inner tube structure, using an external fluid pressure source (not shown) connected to a fluid communication system (not shown), which comprises an external threading sized and adapted to engage the internal threading 90 of port 85, threadingly engaged with port 85. At this point, a pressure sealing operation is performed. In this operation, fluid flow out of the Ported MPT through port 85 of ported cap 8 attached to the upper end 35 of outer tube 3 is prevented. This may be accomplished, for example, by manipulation, either manual or automated, of a flow control device (not shown), such as a valve, of the fluid communication system attached to port 85, or by disconnecting the fluid communication system attached to port 85 and attaching an externally threaded plug (not shown) into port 85. In one embodiment, the Ported MPT is then heated to "cure" the sample by means as are known in the art.

Upon conclusion of the heat treatment, the Ported MPT can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

In an exemplary operation of a Piston MPT (not shown), an outer tube O-ring 2 is installed in each of two grooves 34 of outer tube 3. In one embodiment, two inner tube sections 4 are cooperatively arranged, i.e., with externally narrower ends 45 disposed proximately and externally wider ends 46 disposed proximately, and mating facings 44 are placed in abutment to form an inner tube structure. The end of the inner tube structure comprising externally narrower ends 45 is inserted into the lower (externally wide) end 36 of internal bore 32 of outer tube 3, whereby the outer tapered surface of the inner tube structure adjoins the surface of tapered internal bore 32 of outer tube 3. In one embodiment, a piston O-ring 6 is installed in each external groove 72 of a first piston 7, and that piston 7 thus equipped is installed into a piston cavity 55 of a first piston cap 5, thereby forming two seals between the piston 7 and the inner surface 50 of the piston cavity 55 of the first piston cap 5. First piston cap 5, containing the piston O-rings 6 equipped piston 7, is then attached onto the lower end 36 of outer tube 3 by means of threaded engagement of interior threads 51 of that piston cap 5 and the exterior threads 33 of outer tube 3, thereby forming a seal between the proximate outer tube O-ring 2 and sealing surface 52 of the piston cap 5. Also thereby, internal bore 60 end 53 of that piston cap 5 contacts the bottom end of the inner tube structure and biases the inner tube structure upward into outer tube 3. Such biasing creates a seal between mating surfaces 44 of inner tube sections 4. In one embodiment, a test sample (not shown) is then placed into the upper end of the inner tube structure, which is disposed within outer tube 3. In one embodiment, a piston O-ring 6 is installed in each external groove 72 of a second piston 7, and that piston 7 thus equipped is installed into piston cavity 55 of a second piston cap 5, thereby forming two seals between the piston 7 and the inner surface 50 of piston cavity 55 of the second piston cap 5. Second piston cap 5, containing the piston O-rings 6 equipped piston 7, is then attached onto the upper end 35 of outer tube 3 by means of threaded engagement of interior threads 51 of piston cap 5 and exterior threads 33 of outer tube 3, thereby forming a seal between the proximate outer tube O-ring 2 and sealing surface 52 of piston cap 5. In one embodiment, a desired fluid pressure is then applied, via port 57 of first piston cap 5, to the bottom surface 19 of its piston 5, using an external fluid pressure source (not shown) connected to a fluid communication system (not shown), which comprises an external threading sized and adapted to engage the internal threading 62 of port 57, threadingly engaged with port 57. In one embodiment, a desired fluid pressure is then applied, via port 57 of second piston cap 5, to the top surface 18 of its piston 5, using an external fluid pressure source (not shown) connected to a fluid communication system (not shown), which comprises an external threading sized and adapted to engage the internal threading 62 of port 57, threadingly engaged with port 57. At this point, in one embodiment, two pressure sealing operations are performed. In one operation, fluid flow out of the Piston MPT through port 57 of lower piston cap 5 is prevented. This may be accomplished, for example, by manipulation, either manual or automated, of a flow control device (not shown), such as a valve, of the fluid communication system attached to port 57, or by disconnecting the fluid communication system attached to port 57 and attaching an externally threaded plug (not shown) into port 57. In another operation, fluid flow out of the Piston MPT through port 57 of upper piston cap 5 is prevented. This may be accomplished, for example, by manipulation, either manual or automated, of a flow control device (not shown), such as a valve, of the fluid communication system attached to port 57, or by disconnecting the fluid communication system attached to port 57 and attaching an externally threaded plug (not shown) into port 57. In one embodiment, the Piston MPT is then heated to "cure" the sample by means as are known in the art.

Upon conclusion of the heat treatment, the Piston MPT can be disassembled in the reverse order as described above, for example, and the test sample can be recovered from the inner tube structure for testing. In one embodiment, after curing the test sample, a rubber or wooden mallet is used to force the inner tube structure containing the cured test sample from outer tube 3. The inner tube sections 4 of the inner tube structure can then readily be separated to permit extraction of the set, intact test sample for physical testing.

As one skilled in the art would understand, the operational parameters described above are merely exemplary and be may be modified to fit various applications. The Multi-Purpose Tubes described herein may be employed using various combinations of the operational steps disclosed herein, as for example, with regard to the interchangeability of caps, the means of introducing sample into the inner tube structure, and the sealing and/or pressurization of the sample within the inner tube structure.

Method

In one embodiment, MPT apparatuses described herein are useful for providing a mechanism for allowing liquid test samples to solidify under controlled pressure and temperature conditions, i.e., "set" or "cure," and then isolating the so produced solid material in substantially intact form. The solid material can then be subjected to various material testing procedures to measure certain physical properties thereof. Such physical properties include, but are not limited to, density, permeability, free fluid, compressive strength, mechanical properties, and solid suspending properties.

In one embodiment, a liquid test sample provided to the MPT apparatus comprises a cement slurry. In various embodiments, the cement slurry may comprise, but is not limited to, a foam Portland cement, a non-foam Portland cement, a non-Portland cement, or blends thereof. The invention is not so limited, however, and other cement materials, as well as non-cement materials, may be utilized as test samples for employment of embodiments of the present invention.

Figure 11:
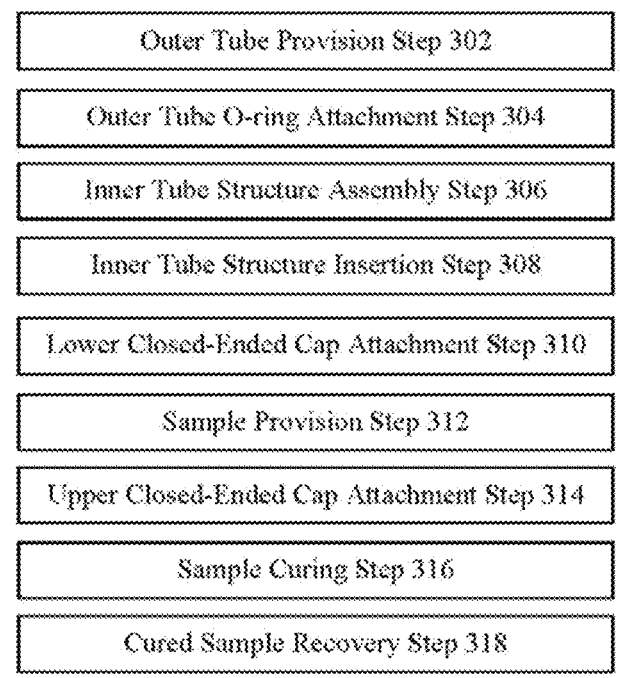
FIG. 11 shows the steps of an embodiment of a method of use of a Sealed MPT of the present invention.

An exemplary method 300 of curing a foam cement sample utilizing an embodiment of a Sealed MPT 100 of the present invention is outlined in FIG. 11, and includes the following steps.

An Outer Tube Provision Step 302, comprising providing an outer tube, such as outer tube 3.

An Outer Tube O-ring Attachment Step 304, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 306, comprising cooperatively arranging a plurality of inner tube sections, such as inner tube sections 4, to form an inner tube structure.

An Inner Tube Structure Insertion Step 308, comprising inserting the inner tube structure into outer tube 3 through the lower end thereof.

A Lower Closed-Ended Cap Attachment Step 310, comprising attaching a closed-ended cap, such as closed-ended cap 1, to the lower end of outer tube 3 equipped with O-ring 2. In one embodiment, such attachment comprises engaging internal threading of closed-ended cap 1, such as internal threading 11, with external threading of outer tube 3, such as external threading 33.

A Sample Provision Step 312, comprising providing a liquid foam cement sample into the upper end of the inner tube structure.

An Upper Closed-Ended Cap Attachment Step 314, comprising attaching a closed-ended cap, such as closed-ended cap 1, to the upper end of outer tube 3 equipped with O-ring 2. In one embodiment, such attachment comprises engaging internal threading of closed-ended cap 1, such as internal threading 11, with external threading of outer tube 3, such as external threading 33.

A Sample Curing Step 316, comprising exposing the Sealed MPT 100 to a desired temperature for a desired period of time.

A Cured Sample Recovery Step 318, comprising disassembling the Sealed MPT 100 and removing the cured sample therefrom.

Figure 12:
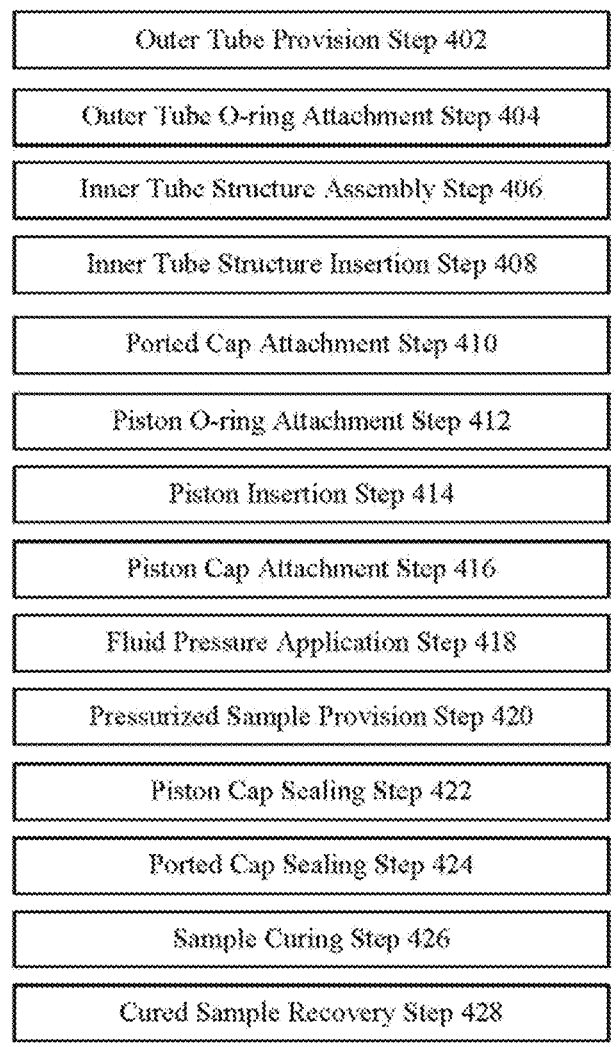
FIG. 12 shows the steps of an embodiment of a method of use of a Ported-Piston MPT of the present invention.

An exemplary method 400 of curing a foam cement sample utilizing an embodiment of a Ported-Piston MPT 200 of the present invention is outlined in FIG. 12, and includes the following steps.

An Outer Tube Provision Step 402, comprising providing an outer tube, such as outer tube 3.

An Outer Tube O-ring Attachment Step 404, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 406, comprising cooperatively arranging a plurality of inner tube sections, such as inner tube sections 4, to form an inner tube structure.

An Inner Tube Structure Insertion Step 408, comprising inserting the inner tube structure into outer tube 3 through the lower end thereof.

A Ported Cap Attachment Step 410, comprising attaching a ported cap, such as ported cap 8, to the lower end of outer tube 3 equipped with O-ring 2. In one embodiment, such attachment comprises engaging internal threading of ported cap 8, such as internal threading 81, with external threading of outer tube 3, such as external threading 33.

A Piston O-ring Attachment Step 412, comprising attaching two O-rings, such as O-rings 6, to a piston, such as piston 7. In one embodiment, such O-ring attachment comprises seating each O-ring 6 in an external outer groove of piston 7, such as groove 72.

A Piston Insertion Step 414, comprising inserting piston 7 equipped with O-rings 6 into a piston cavity, such as piston cavity 55, of a piston cap, such as piston cap 5.

A Piston Cap Attachment Step 416, comprising attaching piston cap 5 containing piston 7 equipped with piston O-rings 6 to the upper end of outer tube 3 equipped with O-ring 2. In one embodiment, such attachment comprises engaging internal threading of piston cap 5, such as internal threading 51, with external threading of outer tube 3, such as external threading 33.

A Fluid Pressure Application Step 418, comprising providing pressurized fluid to the top surface of piston 7 via a port in piston cap 5, such as port 57.

A Pressurized Sample Provision Step 420, comprising providing a pressurized liquid foam cement sample into the inner tube structure via a port in ported cap 8, such as port 85.

A Piston Cap Sealing Step 422, comprising preventing fluid flow out of Ported-Piston MPT 200 through port 57 of piston cap 5.

A Ported Cap Sealing Step 424, comprising preventing fluid flow out of Ported-Piston MPT 200 through port 85 of ported cap 8.

A Sample Curing Step 426, comprising exposing the Ported-Piston MPT 200 containing the sample to a desired temperature for a desired period of time.

A Cured Sample Recovery Step 428, comprising disassembling the Ported-Piston MPT 200 and removing the cured sample therefrom.

Figure 13:
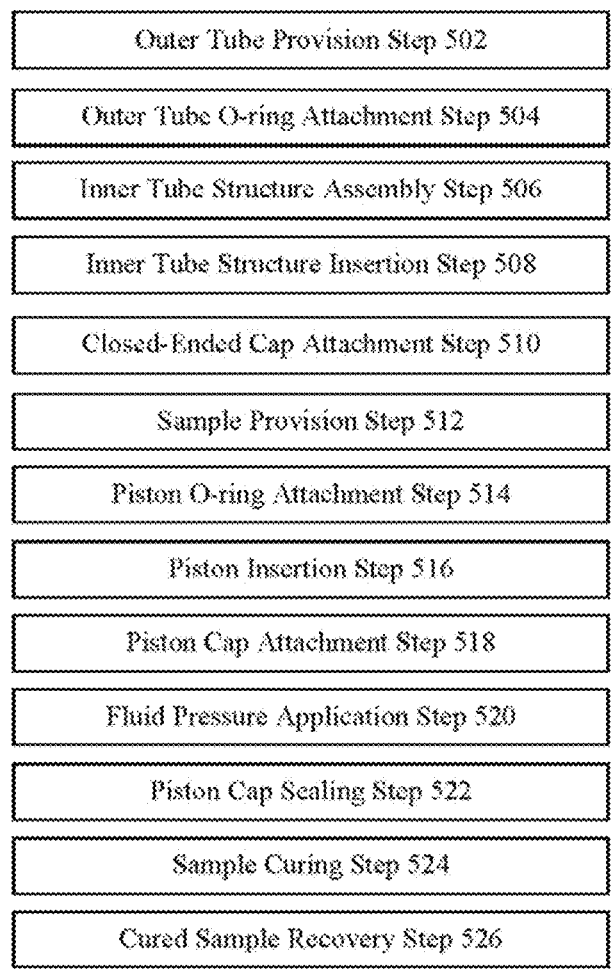
FIG. 13 shows the steps of an embodiment of a method of use of a Piston-Sealed MPT of the present invention.

An exemplary method 500 of curing a foam cement sample utilizing an embodiment of a Piston-Sealed MPT of the present invention is outlined in FIG. 13, and includes the following steps.

An Outer Tube Provision Step 502, comprising providing an outer tube, such as outer tube 3.

An Outer Tube O-ring Attachment Step 504, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 506, comprising cooperatively arranging a plurality of inner tube sections, such as inner tube sections 4, to form an inner tube structure.

An Inner Tube Structure Insertion Step 508, comprising inserting the inner tube structure into outer tube 3 through the lower end thereof.

A Closed-Ended Cap Attachment Step 510, comprising attaching a closed-ended cap, such as closed-ended cap 1, to the lower end of outer tube 3 equipped with O-ring 2. In one embodiment, such attachment comprises engaging internal threading of closed-ended cap 1, such as internal threading 11, with external threading of outer tube 3, such as external threading 33.

A Sample Provision Step 512, comprising providing a liquid foam cement sample into the upper end of the inner tube structure.

A Piston O-ring Attachment Step 514, comprising attaching two O-rings, such as O-rings 6, to a piston, such as piston 7. In one embodiment, such O-ring attachment comprises seating each O-ring 6 in an external outer groove of piston 7, such as groove 72.

A Piston Insertion Step 516, comprising inserting piston 7 equipped with O-rings 6 into a piston cavity, such as piston cavity 55, of a piston cap, such as piston cap 5.

A Piston Cap Attachment Step 518, comprising attaching piston cap 5 containing piston 7 equipped with piston O-rings 6 to the upper end of outer tube 3 equipped with O-ring 2. In one embodiment, such attachment comprises engaging internal threading of piston cap 5, such as internal threading 51, with external threading of outer tube 3, such as external threading 33.

A Fluid Pressure Application Step 520, comprising providing pressurized fluid to the top surface of piston 7 via a port in piston cap 5, such as port 57.

A Piston Cap Sealing Step 522, comprising preventing fluid flow out of the Piston-Sealed MPT through port 57 of piston cap 5.

A Sample Curing Step 524, comprising exposing the Piston-Sealed MPT containing the sample to a desired temperature for a desired period of time.

A Cured Sample Recovery Step 526, comprising disassembling the Piston-Sealed MPT and removing the cured sample therefrom.

Figure 14:
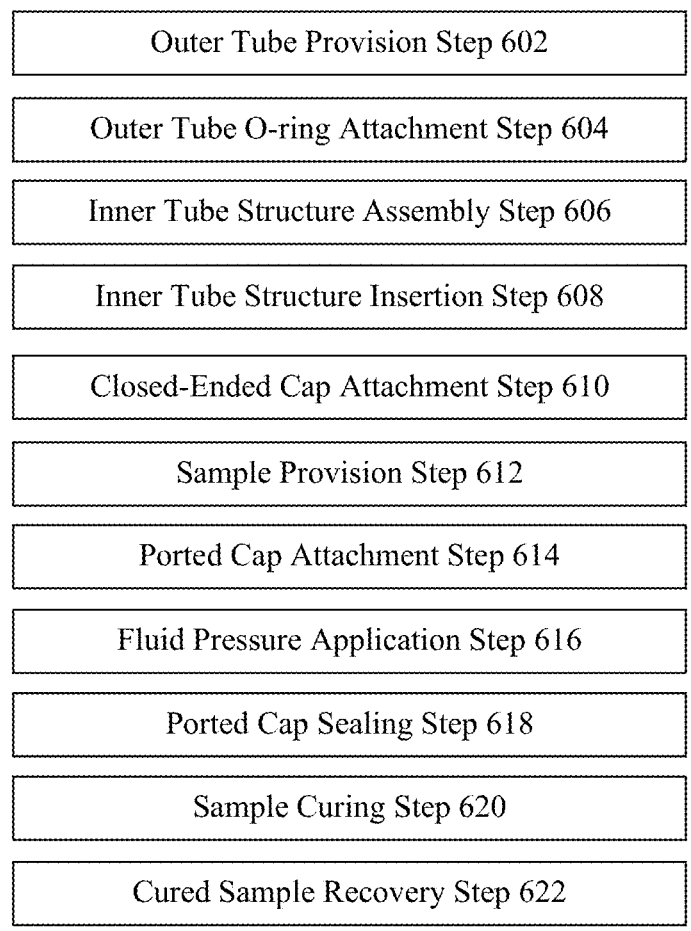
FIG. 14 shows the steps of an embodiment of a method of use of a Ported-Sealed MPT of the present invention.

An exemplary method 600 of curing a foam cement sample utilizing an embodiment of a Ported-Sealed MPT of the present invention is outlined in FIG. 14, and includes the following steps.

An Outer Tube Provision Step 602, comprising providing an outer tube, such as outer tube 3.

An Outer Tube O-ring Attachment Step 604, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 606, comprising cooperatively arranging a plurality of inner tube sections, such as inner tube sections 4, to form an inner tube structure.

An Inner Tube Structure Insertion Step 608, comprising inserting the inner tube structure into outer tube 3 through the lower end thereof.

A Closed-Ended Cap Attachment Step 610, comprising attaching a closed-ended cap, such as closed-ended cap 1, to the lower end of outer tube 3 equipped with O-ring 2. In one embodiment, such attachment comprises engaging internal threading of closed-ended cap 1, such as internal threading 11, with external threading of outer tube 3, such as external threading 33.

A Sample Provision Step 612, comprising providing a liquid foam cement sample into the inner tube structure via a port in ported cap 8, such as port 85.

A Ported Cap Attachment Step 614, comprising attaching a ported cap, such as ported cap 8, to the upper end of outer tube 3 equipped with O-ring 2. In one embodiment, such attachment comprises engaging internal threading of ported cap 8, such as internal threading 81, with external threading of outer tube 3, such as external threading 33.

A Fluid Pressure Application Step 616, comprising providing pressurized fluid to the inner tube structure via a port in ported cap 8, such as port 85.

A Ported Cap Sealing Step 618, comprising preventing fluid flow out of the Ported-Sealed MPT through port 85 of ported cap 8.

A Sample Curing Step 620, comprising exposing the Ported-Sealed MPT containing the sample to a desired temperature for a desired period of time.

A Cured Sample Recovery Step 622, comprising disassembling the Ported-Sealed MPT and removing the cured sample therefrom.

Figure 15:
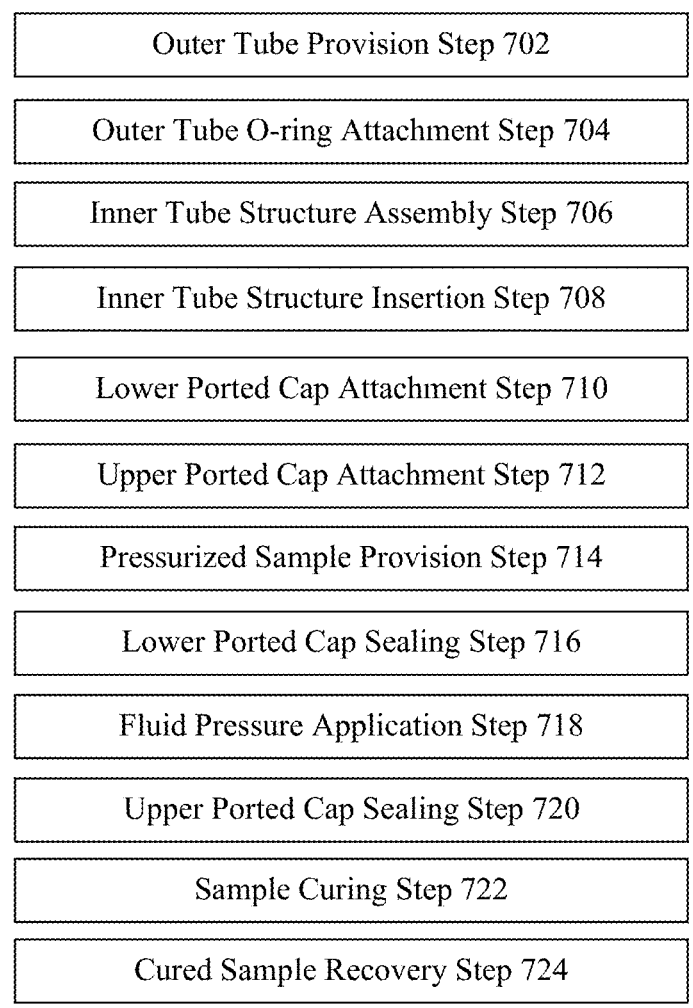
FIG. 15 shows the steps of an embodiment of a method of use of a Ported MPT of the present invention.

An exemplary method 700 of curing a foam cement sample utilizing an embodiment of a Ported MPT of the present invention is outlined in FIG. 15, and includes the following steps.

An Outer Tube Provision Step 702, comprising providing an outer tube, such as outer tube 3.

An Outer Tube O-ring Attachment Step 704, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 706, comprising cooperatively arranging a plurality of inner tube sections, such as inner tube sections 4, to form an inner tube structure.

An Inner Tube Structure Insertion Step 708, comprising inserting the inner tube structure into outer tube 3 through the lower end thereof.

A Lower Ported Cap Attachment Step 710, comprising attaching a ported cap, such as ported cap 8, to the lower end of outer tube 3 equipped with O-ring 2. In one embodiment, such attachment comprises engaging internal threading of ported cap 8, such as internal threading 81, with external threading of outer tube 3, such as external threading 33.

An Upper Ported Cap Attachment Step 712, comprising attaching a ported cap, such as ported cap 8, to the upper end of outer tube 3 equipped with O-ring 2. In one embodiment, such attachment comprises engaging internal threading of ported cap 8, such as internal threading 81, with external threading of outer tube 3, such as external threading 33.

A Pressurized Sample Provision Step 714, comprising providing a pressurized liquid foam cement sample into the inner tube structure via a port in lower ported cap 8, such as port 85.

A Lower Ported Cap Sealing Step 716, comprising preventing fluid flow out of the Ported MPT through port 85 of lower ported cap 8.

A Fluid Pressure Application Step 718, comprising providing pressurized fluid to the inner tube structure via a port in upper ported cap 8, such as port 85.

An Upper Ported Cap Sealing Step 720, comprising preventing fluid flow out of the Ported MPT through port 85 of upper ported cap 8.

A Sample Curing Step 722, comprising exposing the Ported MPT containing the sample to a desired temperature for a desired period of time.

A Cured Sample Recovery Step 724, comprising disassembling the Ported MPT and removing the cured sample therefrom.

Figure 16:
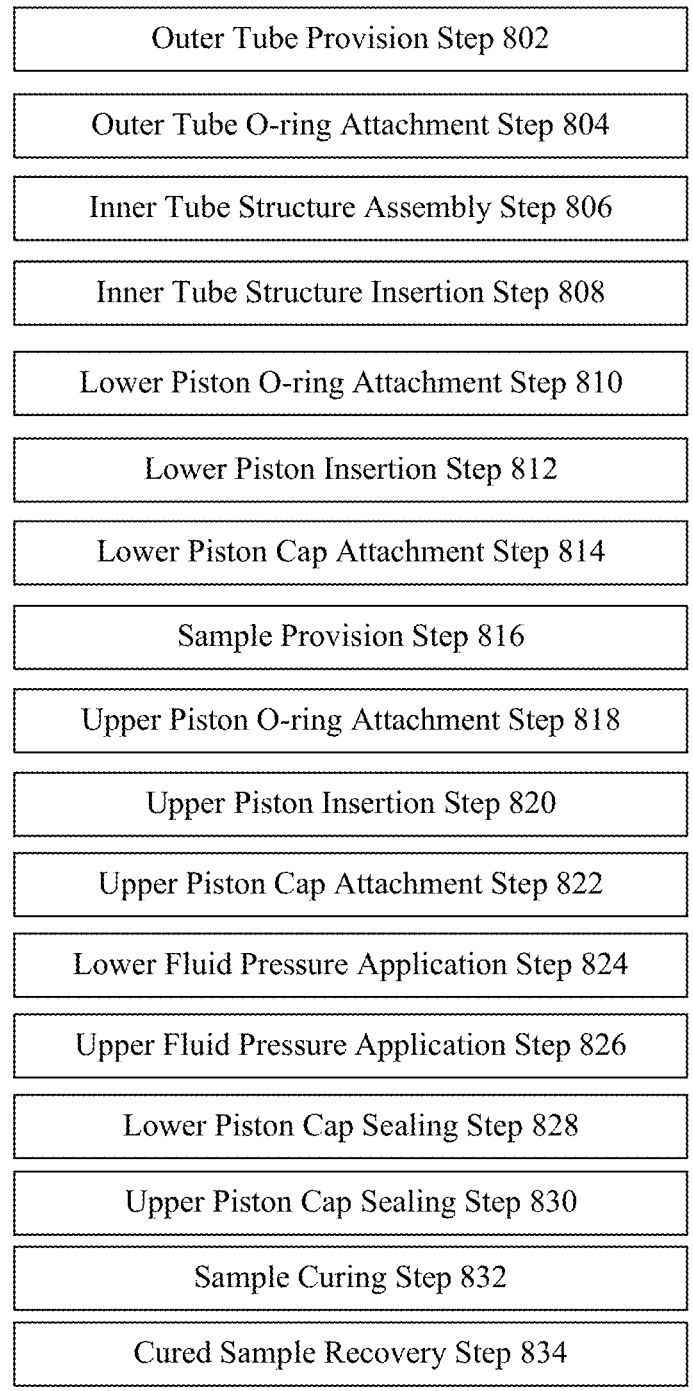
FIG. 16 shows the steps of an embodiment of a method of use of a Piston MPT of the present invention.

An exemplary method 800 of curing a foam cement sample utilizing an embodiment of a Piston MPT of the present invention is outlined in FIG. 16, and includes the following steps.

An Outer Tube Provision Step 802, comprising providing an outer tube, such as outer tube 3.

An Outer Tube O-ring Attachment Step 804, comprising attaching two O-rings, such as O-rings 2, to outer tube 3. In one embodiment, such O-ring attachment comprises seating each O-ring 2 in an external outer groove of outer tube 3, such as groove 34.

An Inner Tube Structure Assembly Step 806, comprising cooperatively arranging a plurality of inner tube sections, such as inner tube sections 4, to form an inner tube structure.

An Inner Tube Structure Insertion Step 808, comprising inserting the inner tube structure into outer tube 3 through the lower end thereof.

A Lower Piston O-ring Attachment Step 810, comprising attaching two O-rings, such as O-rings 6, to a lower piston, such as piston 7. In one embodiment, such O-ring attachment comprises seating each O-ring 6 in an external outer groove of lower piston 7, such as groove 72.

A Lower Piston Insertion Step 812, comprising inserting lower piston 7 equipped with O-rings 6 into a piston cavity, such as piston cavity 55, of a lower piston cap, such as piston cap 5.

A Lower Piston Cap Attachment Step 814, comprising attaching lower piston cap 5 to the lower end 36 of outer tube 3 equipped with O-ring 2. In one embodiment, such attachment comprises engaging internal threading of lower piston cap 5, such as internal threading 51, with external threading of outer tube 3, such as external threading 33.

A Sample Provision Step 816, comprising providing a liquid foam cement sample into the upper end of the inner tube structure.

An Upper Piston O-ring Attachment Step 818, comprising attaching two O-rings, such as O-rings 6, to an upper piston, such as piston 7. In one embodiment, such O-ring attachment comprises seating each O-ring 6 in an external outer groove of upper piston 7, such as groove 72.

An Upper Piston Insertion Step 820, comprising inserting upper piston 7 equipped with O-rings 6 into a piston cavity, such as piston cavity 55, of an upper piston cap, such as piston cap 5.

An Upper Piston Cap Attachment Step 822, comprising attaching upper piston cap 5 to the upper end of outer tube 3 equipped with O-ring 2. In one embodiment, such attachment comprises engaging internal threading of upper piston cap 5, such as internal threading 51, with external threading of outer tube 3, such as external threading 33.

A Lower Fluid Pressure Application Step 824, comprising providing pressurized fluid to the bottom surface, such as bottom surface 19, of lower piston 7 via a port in lower piston cap 5, such as port 57.

An Upper Fluid Pressure Application Step 826, comprising providing pressurized fluid to the top surface, such as top surface 18, of upper piston 7 via a port in upper piston cap 5, such as port 57.

A Lower Piston Cap Sealing Step 828, comprising preventing fluid flow out of the Piston MPT through port 57 of lower piston cap 5.

An Upper Piston Cap Sealing Step 830, comprising preventing fluid flow out of the Piston MPT through port 57 of upper piston cap 5.

A Sample Curing Step 832, comprising exposing the Piston MPT containing the sample to a desired temperature for a desired period of time.

A Cured Sample Recovery Step 834, comprising disassembling the Piston MPT and removing the cured sample therefrom.

As would be understood by one skilled in the art, methods 300, 400, 500, 600, 700, and 800 are only exemplary, and may be modified to accomplish specific results, such modifications including, but not limited to, combining, adding, deleting, re-ordering, and/or repeating one or more steps. As would also be understood by one skilled in the art, while methods 300, 400, 500, 600, 700, and 800 have been described as a plurality of steps, in various embodiments, two or more steps may be performed concurrently.

While the present invention has been disclosed and discussed in connection with the foregoing embodiments, it will be understood that the invention is not limited to the embodiments disclosed, but is capable of numerous rearrangements, modifications, and substitutions of parts and elements without departing from the spirit and scope of the invention.

We claim:
1. A method for testing a sample comprising:
providing a testing apparatus comprising:
  an outer tube;
  a plurality of inner tube sections;
  a ported cap;
  a piston cap; and
  a piston;
  wherein:
    said outer tube comprises a tapered axial internal bore;
    said plurality of inner tube sections is cooperatively longitudinally arranged to form an externally tapered inner tube structure;
    said inner tube structure is disposed within said outer tube;
    said outer tube comprises external threading proximate each end thereof;
    said ported cap comprises:
      an internal bore comprising internal threading proximate an open first end of said ported cap; and
      an internally threaded port which fluidly connects an exterior of a second end of said ported cap to said internal bore of said ported cap;
    said piston cap comprises:
      an internal bore comprising internal threading proximate an open first end of said piston cap;
      a piston cavity within said piston cap internal bore, said piston cavity having an internal diameter substantially equal to an internal diameter of said inner tube structure; and
      an internally threaded port which fluidly connects an exterior of a second end of said piston cap to said piston cavity;
    said piston is disposed within said piston cavity;
    said ported cap is sealingly attached to a first end of said outer tube via engagement of said ported cap internal bore threading and said outer tube external threading; and
  said piston cap is sealingly attached to a second end of said outer tube via engagement of said piston cap internal bore threading and said outer tube external threading;
  providing pressurized fluid to an exterior surface of said piston via said piston cap port, thereby forcing said piston out of said piston cavity to a position in said inner tube structure proximate said ported cap;
  providing a pressurized liquid sample into said inner tube structure via said ported cap port, thereby forcing said piston back into said piston cavity;
  preventing fluid flow out of said apparatus through said piston cap port;
  preventing fluid flow out of said apparatus through said ported cap port;
  exposing said apparatus containing said sample to a desired temperature for a desired period of time to at least partially solidify said sample;
  disassembling said apparatus; and
  recovering said at least partially solidified sample.

2. The method of claim 1, wherein said outer tube comprises an external circumferential groove proximate each said-end thereof, and an elastomer seal is seated in each said outer tube groove.

3. The method of claim 1, wherein said piston comprises one or more circumferential external grooves, and an elastomer seal is disposed in at least one of said one or more piston external grooves.

4. The method of claim 1, wherein said sample comprises a cement.

5. The method of claim 4, wherein said cement is selected from the group consisting of:
foam Portland cement;
non-foam Portland cement;
non-Portland cement; and
combinations thereof.

* * * * *